(12) United States Patent
Yates

(10) Patent No.: US 8,413,275 B1
(45) Date of Patent: Apr. 9, 2013

(54) BACK RELAXING DEVICE

(76) Inventor: Patrick Dale Yates, Grass Valley, CA (US)

( * ) Notice: Subject to any disclaimer, the term of this patent is extended or adjusted under 35 U.S.C. 154(b) by 0 days.

(21) Appl. No.: 13/344,525

(22) Filed: Jan. 5, 2012

(51) Int. Cl.
*A61G 15/00* (2006.01)
(52) U.S. Cl. ..................................... 5/652; 5/632; 5/633
(58) Field of Classification Search ............... 5/632–633, 5/630, 652, 653.1
See application file for complete search history.

(56) References Cited

U.S. PATENT DOCUMENTS 4,230,099 A * 10/1980 Richardson .................. 606/240

* cited by examiner

*Primary Examiner* — Fredrick Conley
(74) *Attorney, Agent, or Firm* — Oakwood Law Group, LLP; Jie Tan

(57) ABSTRACT

An easy back relaxing device. The device has three contour sections along the vertical axis and three contour sections long the horizontal axis. Along the vertical axis, one section is shaped to match and support a human lumbar spine, one section is shaped to match and support a human thoracic spine, and one section is shaped to match and support a human cervical spine. Along the horizontal axis, two side sections are for back aliment, and the middle section is lightly protruding for exerting pressure on spine hot points.

4 Claims, 4 Drawing Sheets

BACK RELAXING DEVICE

DESCRIPTION OF RELATED ART

The present application relates to a back relaxing device, and more particularly to a device that is designed to allow natural back stretching with pressure exertion on key spinal points.

Note that the points discussed below may reflect the hindsight gained from the disclosed inventions, and are not necessarily admitted to be prior art.

Back pain has been very common among office workers. Whether it's from a simple muscle strain or a result of a spinal condition, back pain can seriously affect your life.

Although there are many ways in which back pain can develop, physicians and other medical experts have outlined several common causes of pain in the back and spinal cord. These most notable include, for example, lumbar muscle strain, where a lower back muscle spasms are experienced. The strain generally occurs when the muscle fibers are abnormally stretched or torn; a sprain occurs when ligaments are torn from their attachments. Herniated disc, is another common source of back pain when a spinal disc ruptures and bulges outside of its normal boundary. The rupture can be caused by an accident, fall, or repeated straining. Discogenic back pain is associated with degeneration of the lumbar discs with the aging process. Also some of the most common spinal diseases include spinal stenosis, lumbar spine arthritis, spondylolisthesis, and osteoporosis, are associated with excruciating back pain.

However, statistics show that 90% of all back surgeries are not necessary. A good stretching routine can alleviate many causes of back pain. There are many commercially available massaging devices as well as stretching devices for helping with back relaxing. For example, US Patent Application Publication 2011/0105968 A1 describes a device design with a string of balls that can selectively massage certain muscle points on the back. Another US Patent Publication U.S. Pat. No. 5,411,471 A describes a device mainly for neck relaxing that has a back support section with a matching shape to the back. These designs are either not for the back stretching or does not allow muscle relax by stretching.

SUMMARY

The present application discloses novel, simple, effective and affordable back relaxing device that performs both natural key point spinal pressing and naturally back stretching of the body.

In one embodiment, a back stretching device includes a shovel-shaped body that has crown curvature that matches the curvature of the back spine. The surface curvature includes three sections with one section matches the curvature of the lumbar spine, one section matches to the curvature of the thoracic spine and one section matches to the cervical spine curvature.

In one aspect of an embodiment, the horizontal surface comprises three curvature sections to match the curvature of a human back. The left and right curvature surfaces keep body aliment, and the middle section is for spinal support, which is configured to be a protrusion to exert pressure on lumber spine key points.

The disclosed innovation is lightweight, durable, and portable and cost effective device. It can be used for sitting up as well as relaxing back muscles.

BRIEF DESCRIPTION OF THE DRAWINGS

The disclosed application will be described with reference to the accompanying drawings, which show important sample embodiments of the invention and which are incorporated in the specification hereof by reference, wherein.

DETAILED DESCRIPTION OF SAMPLE EMBODIMENTS

Figure 1:
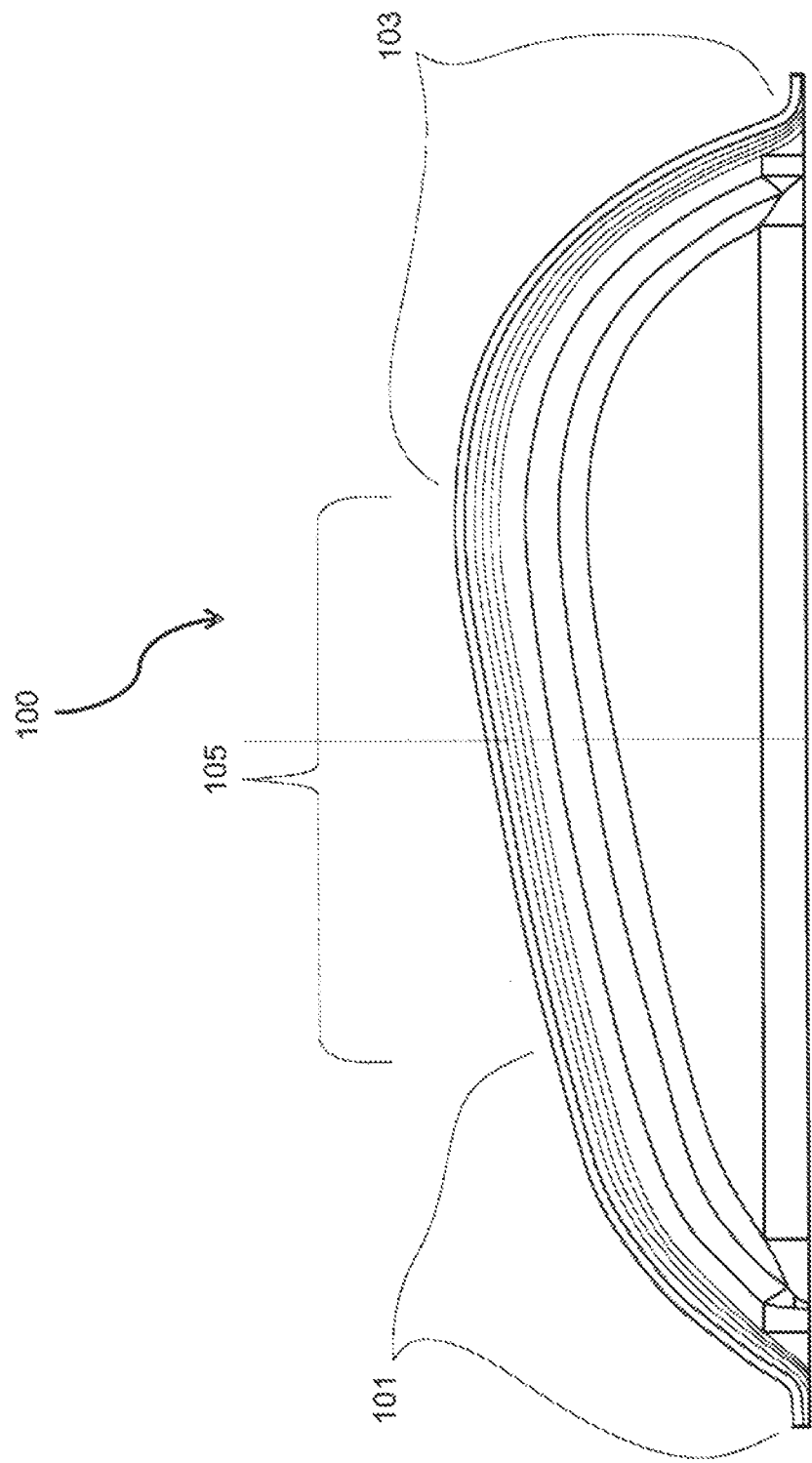
FIG. 1 is a section view along the vertical axis of an example easy back relaxer in accordance with this application.

The numerous innovative teachings of the present application will be described with particular reference to presently preferred embodiments (by way of example, and not of limitation). The present application describes several embodiments, and none of the statements below should be taken as limiting the claims generally.

For simplicity and clarity of illustration, the drawing figures illustrate the general manner of construction, and description and details of well-known features and techniques may be omitted to avoid unnecessarily obscuring the invention. Additionally, elements in the drawing figures are not necessarily drawn to scale, some areas or elements may be expanded to help improve understanding of embodiments of the invention.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

It is contemplated and intended that the design apply to any suitable material, preferably plastic, it may also be made of wood, rubber, plexiglass etc.

In reference to FIG. 1, an example BackTRAX™ stretching and relaxation device 100 is an elongated shovel-shaped body support accommodating a person to lay the back against it and stretch and relax the back muscle. Along the vertical axis, the surface is shaped with three sections of curvatures. Section 103 is shaped to match and support the lumbar spinal section of the back, it has deeper contour to allow the muscles along the lumbar spinal region to naturally relax with gravity. Section 105 and section 101 are configured to match and support the upper back and the neck, allowing the thoracic spine and the cervical spine curvature to naturally stretch and relax with gravity.

Figure 2:
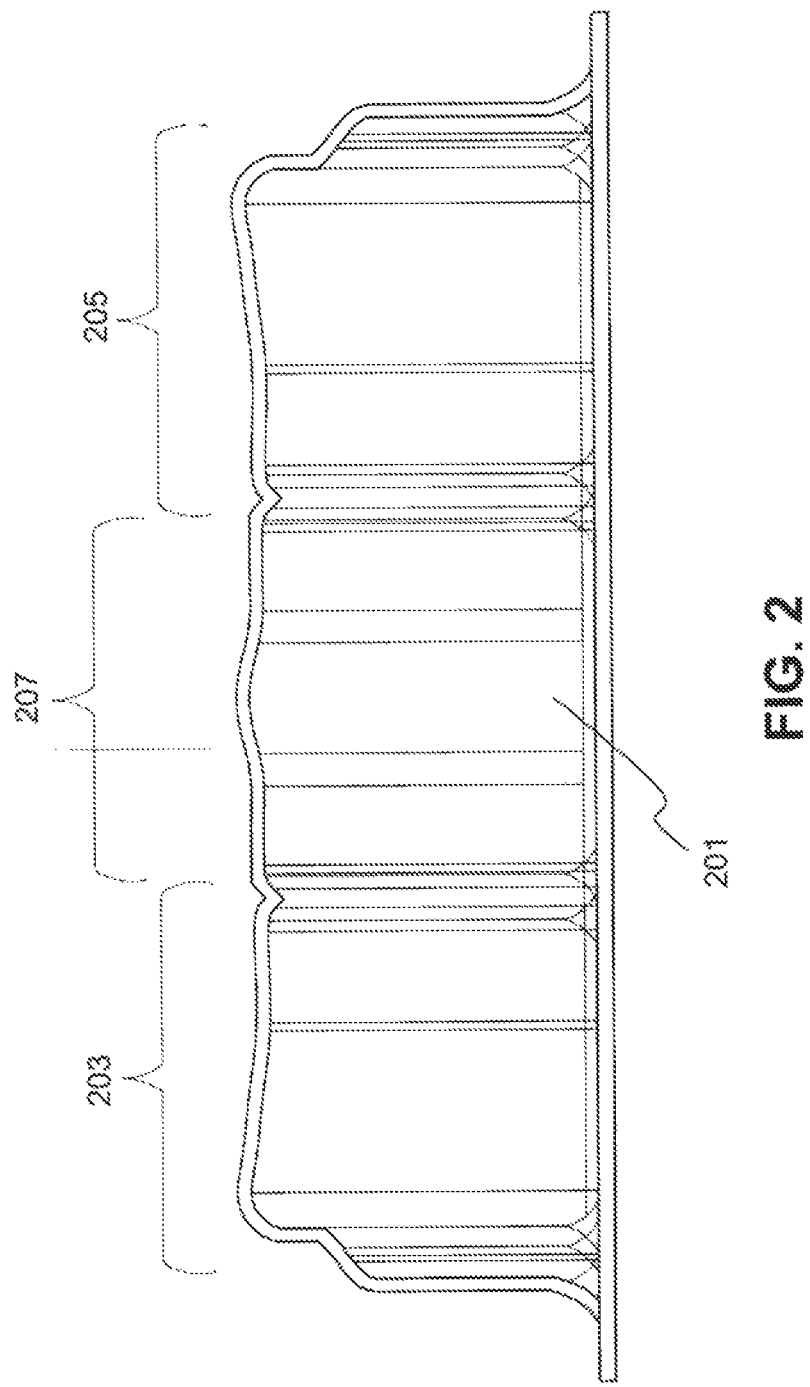
FIG. 2 is a section view along the horizontal axis of an example easy back relaxer in accordance with this application.

In reference to FIG. 2, an example BackTRAX™ stretching and relaxation device is also configured to match the shape of the back contour. The surface along the horizontal axis includes three curvature sections, section 203 and section 205 are on the left and right side of the surface, they are slightly curved to keep body aliment. Section 207 is configured to have a slight protrude area 201 which is to exert pressure for the spine.

Figure 3:
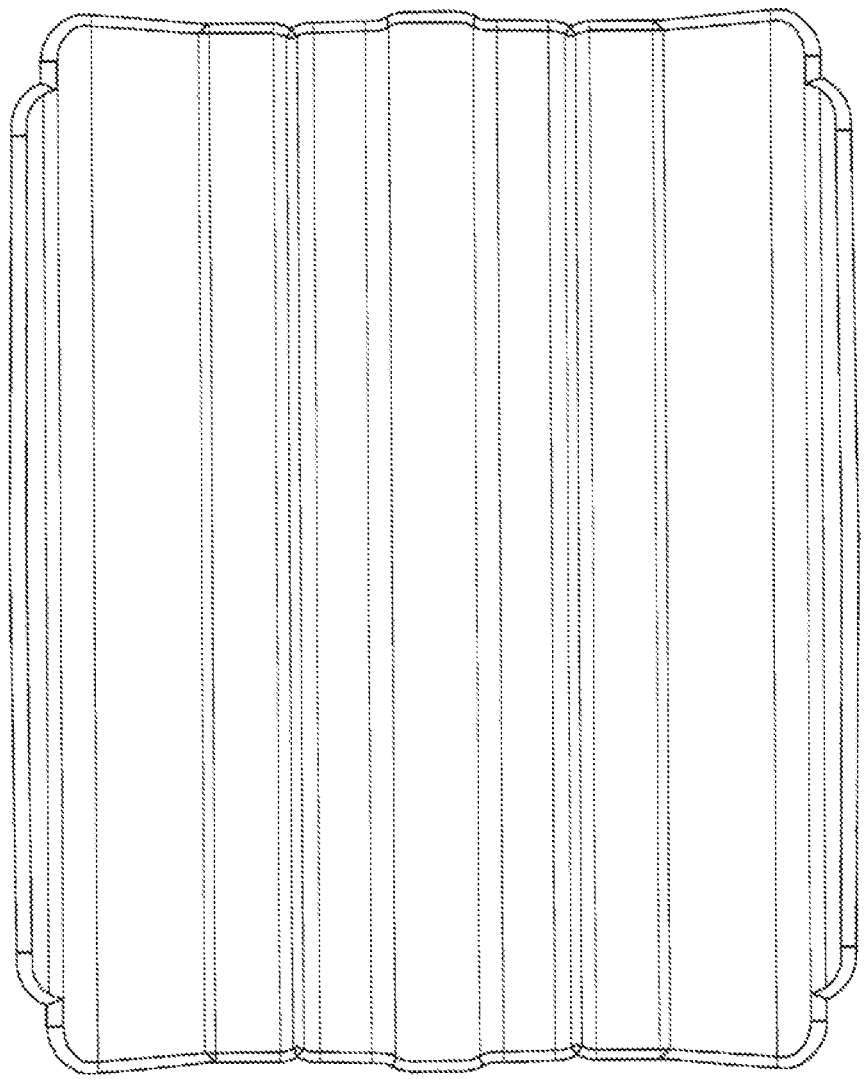
FIG. 3 is a top view of an example easy back relaxer in accordance with this application.
Figure 4:
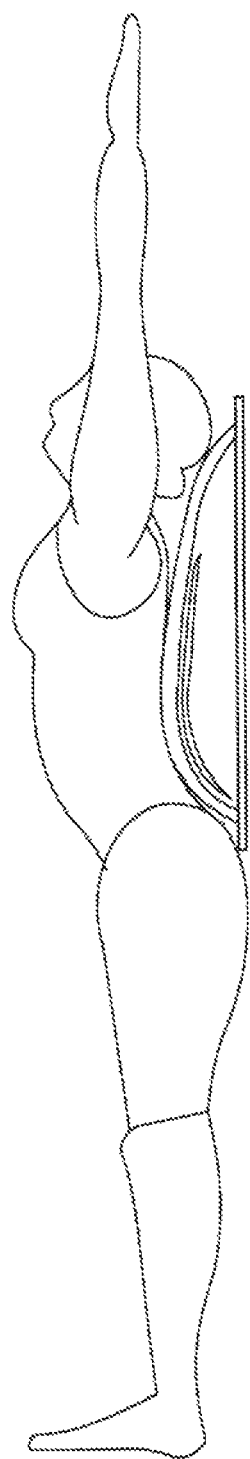
FIG. 4 schematically demonstrates the use of an example easy back relaxer in accordance with this application.

In reference to FIG. 3, protrusion area 201 is extended along the middle axis of the device to exert pressure along the whole spine curvature as shown in FIG. 4. An example Back-TRAX™ back stretching and relaxing device is lightweight, durable and portable that can withstand up to 400 pounds. It can be used to lay with the lower back on the largest part of the curve for low back pain, with the lowest part of curve for upper back pain. Preferably the upper back side is used before using the lower back side as it is a gentler stretch. It also can be used for modified sit-ups, providing support for the lower back while strengthening the back and abdominal muscles as well as for "bench pressing" light weights to work on the shoulder, arm and chest muscles.

The device is one single, durable piece with no detachable or moving parts, lightweight and portable, can be packed it in the suitcase and taken anywhere. The specific ridges and pressure points are created to realign the spine, decompress and hydrate the discs, and allow the spine and surrounding muscles to fully stretch and relax.

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A back relaxing device, comprising:
   a back support body having a vertical axis and a horizontal axis;
   a first curvature section, a second curvature section and a third curvature section being configured along the vertical axis;
   said horizontal axis spanning said back support body in full, consisting of a fourth curvature section, a fifth curvature section and a sixth curvature section;
   wherein said fifth curvature section is configured in between said fourth curvature section and said sixth curvature section; and said fourth curvature section being substantially symmetrical to said sixth curvature section along a middle vertical axis in said fifth curvature section; and said fourth, fifth and sixth curvature sections are substantially horizontally leveled,
   wherein said first curvature section is configured to match and support a human lumbar spine, said second curvature section is configured to match and support a human thoracic spine, and said third curvature section is configured to match and support a human cervical spine, wherein said fourth and said sixth curvature sections concavely curved towards said fifth curvature section, and said fifth curvature is symmetrically and convexly configured around said middle vertical axis forming a gentle protruding to exert pressure on a spine.

2. The back relaxing device of claim 1, said back support body is made of rubber.

3. The back relaxing device of claim 1, said back support body is one piece.

4. The back relaxing device of claim 1, said back support body is made of plastic.

* * * * *